US010995009B2

(12) United States Patent
Papile

(10) Patent No.: US 10,995,009 B2
(45) Date of Patent: May 4, 2021

(54) RENEWABLE ENERGY PRODUCED AMMONIA, APPARATUS, METHOD AND MATERIALS

(71) Applicant: Christopher Papile, Blackstone, MA (US)

(72) Inventor: Christopher Papile, Blackstone, MA (US)

( * ) Notice: Subject to any disclaimer, the term of this patent is extended or adjusted under 35 U.S.C. 154(b) by 0 days.

(21) Appl. No.: 16/681,176

(22) Filed: Nov. 12, 2019

(65) Prior Publication Data

US 2020/0148547 A1 May 14, 2020

Related U.S. Application Data

(60) Provisional application No. 62/758,668, filed on Nov. 11, 2018.

(51) Int. Cl.

| C01C 1/04 | (2006.01) |
| C07C 273/04 | (2006.01) |
| F03G 6/06 | (2006.01) |
| C25B 1/04 | (2021.01) |
| F28D 20/00 | (2006.01) |

(52) U.S. Cl.
CPC .............. *C01C 1/04* (2013.01); *C01C 1/0405* (2013.01); *C07C 273/04* (2013.01); *C25B 1/04* (2013.01); *F03G 6/064* (2013.01); *F28D 20/0034* (2013.01); *F28D 2020/0047* (2013.01)

(58) Field of Classification Search
None
See application file for complete search history.

(56) References Cited

U.S. PATENT DOCUMENTS

| 10,584,422 | B1* | 3/2020 | Yang | C25B 15/08 |
| 2006/0065545 | A1* | 3/2006 | Balan | C25B 1/04 |
| | | | | 205/628 |
| 2010/0003184 | A1* | 1/2010 | Nakamura | C01B 13/0207 |
| | | | | 423/359 |
| 2012/0100062 | A1* | 4/2012 | Nakamura | C01B 3/042 |
| | | | | 423/359 |
| 2013/0039833 | A1* | 2/2013 | Zullo | C05C 3/00 |
| | | | | 423/359 |

(Continued)

*Primary Examiner* — Wayne A Langel
(74) *Attorney, Agent, or Firm* — Lambert Shortell & Connaughton; David J. Connaughton, Jr.; Gary E. Lambert

(57) ABSTRACT

The production of $NH_3$, Urea, UAN, and DAP, starting from inherently intermittent renewable energy, such as photovoltaic and wind power, is made economical by use of molten salt thermal energy storage (ESS) and water electrolyzer (WE) concentrated oxygen. The process inputs and equipment apply air; hydrogen-containing fuel, such as biomass; WE (concentrated $O_2$ and $H_2$ producing); thermal ESS equipped with a turbine and generator to steady the electricity input to the WE; and an ammonia plant. The thermal ESS enables minimally sized process equipment including, the WE, the air separation unit and less hydrogen storage. The concentrated oxygen from the water electrolyzer uniquely enables high-temperature thermal ESS input, water and CO2 collection and other fertilizer products, including Urea, UAN and DAP. DAP production is facilitated by using WE high-purity $O_2$ oxidation and ammonium nitrate is similarly facilitated by anhydrous $NH_3$ oxidation.

11 Claims, 2 Drawing Sheets

(56) References Cited

U.S. PATENT DOCUMENTS

Figure 1:
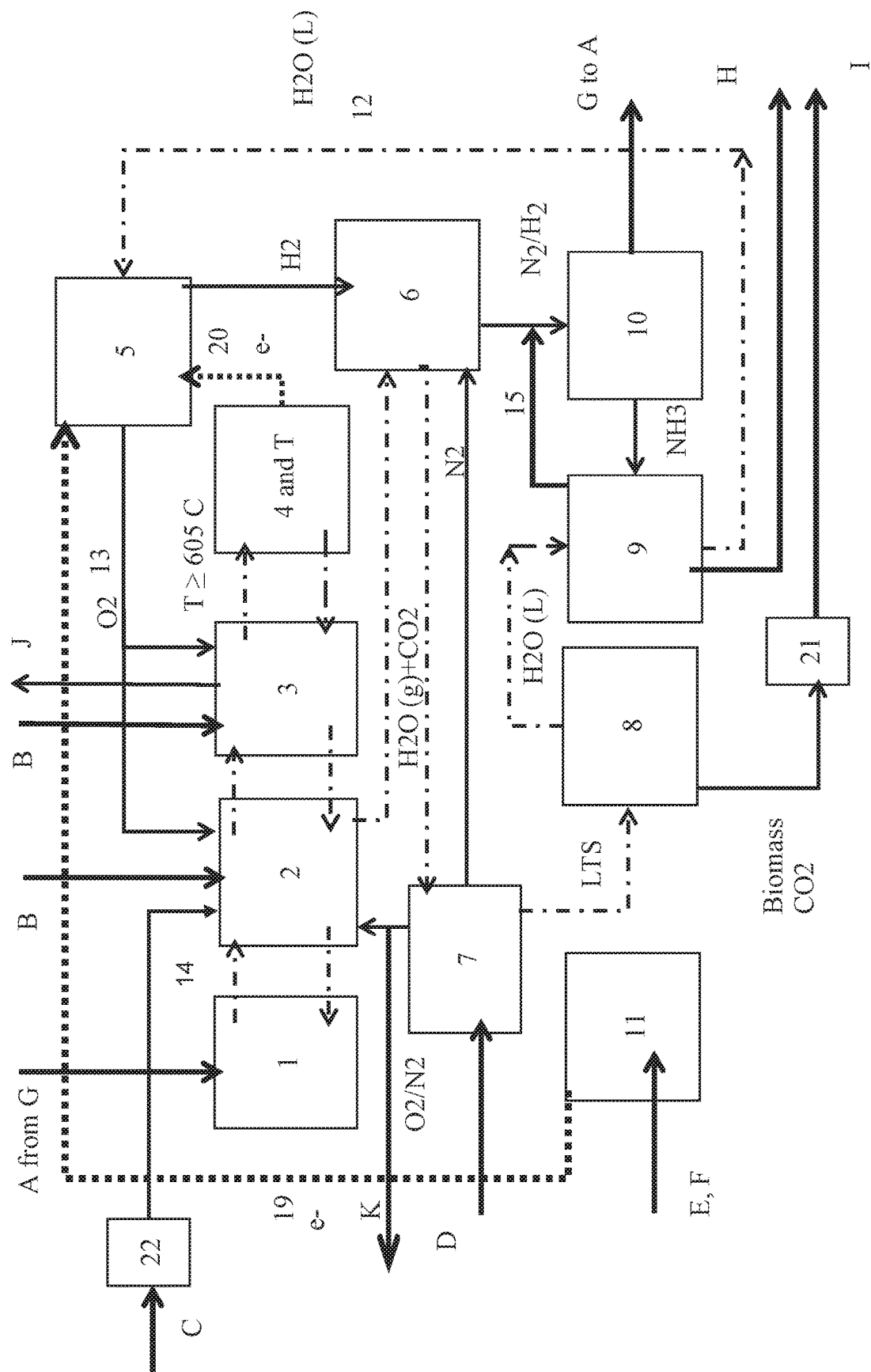

2016/0369411 A1* 12/2016 Handagama ............ C25B 15/08
2017/0122129 A1* 5/2017 Heid ................... C01B 13/0207
2017/0145915 A1* 5/2017 Heid ................... C01B 13/0207

* cited by examiner

RENEWABLE ENERGY PRODUCED AMMONIA, APPARATUS, METHOD AND MATERIALS

FIELD

The subject matter herein is related to producing $NH_3$, Urea, UAN and DAP from intermittent renewable energy, water and phosphorous, $O_2$ and $H_2$ derived from water electrolysis, $N_2$ derived from an air separator and supplementary electricity and steam derived from molten salt thermal energy storage system.

BACKGROUND

The best placement of photovoltaic power modules is often in locations that are inland that may have various ammonia producing restrictions, such as, process water may be costly or scarce, natural gas and naphtha may not be available, and ambient temperature may be high (35 to 50° C.).

Ammonia price premiums, between coastal and inland due to over-ground transport cost are significant, for example, USA Midwest 405 USD/MT NH3 (due to over-ground transport costs) compared with US Gulf Coast prices of 250 USD. The shipment cost of ammonia does not necessarily decrease with ammonia prices, so that during low ammonia price market times, the shipment costs becomes a greater percentage of the overall cost burden.

A second degree of restriction is, if photovoltaic (PV) and/or wind power is used to make ammonia they are intermittent power sources (short-term dependent supply) as are most renewables. When wind is the primary source, often ambient temperature is not an issue, so solar power combined with wind may provide more stability, but the intermittent nature of wind power is restrictive for use in producing chemical products.

Recently an analysis done by the Kenyan government and a Japanese multinational looked into installing a local fertilizer plant in Kenya was put on hold, because it was decided that it did not make economic sense due to Kenya's lack of the raw materials to make ammonia.

Production of $CO_2$-negative-or-neutral ammonia would empower African economies that lack natural gas and petroleum and have fragile water supplies.

SUMMARY

The present disclosure addresses how to produce $CO_2$-negative or $CO_2$-neutral, eco-friendly ammonia within the restrictions placed by the producer's location, which may include: no night photovoltaic power supply, water scarcity or high price, lack of natural gas or lack of will to use natural gas or naphtha, and high ambient temperature.

This engineering innovation is described in detail below. Some features include: renewable energy, such as photovoltaic (PV)+ thermal energy storage, such as molten salt energy storage (ESS) with steam turbine electricity generators+ water electrolysis (WE), such as PEM, AWE or solid oxide+ using the $O_2$ from the WE and additional pressure swing adsorption (PSA) or cryogenic air separation unit (ASU) exhaust for enriched oxygen steam generator+a small-scale ammonia plant+ UAN production on location.

The process produces simultaneously its own $H_2O$ for feed to the WE from enriched oxygen combustion, where the $O_2$ for the combustion is derived from the WE. In one embodiment the process uses biomass combustion heat to load a molten salt energy storage device (usually used in CSP) to make electricity, when the PV system cannot operate due to lack of sunlight, thus allowing the electrolyzer, ASU and possibly PV system to remain minimally sized.

Molten salt thermal energy storage comes in a variety of forms, including, one tank (hot fluid on top and barrier separated cooler fluid on the bottom) and two tanks, in which hot and heat-dissipated forms of the molten salt are separated. Higher temperature molten salt provides more efficient conversion of heat to electricity. Commercial molten salts such as Hitec and Hitec XL provide high temperatures up to 538° C. which enables a practical embodiment, but does not take full advantage of the high temperature combustion quality of concentrated oxygen, for which molten salts can operate above 1025 F (>560° C.).

An example nitrate molten salt that has a high temperature window, is 44% $Ca(NO_3)_2$/12% $NaNO_3$/44% $KNO_3$ (use window: 127.6 min-620° C. max); a two component Nitrate salt mixture, for example, 40% $KNO_3$ 60% $NaNO_3$, can operate up to 600° C. Practical high inlet temperatures applied to ultra-super critical and supercritical pressure steam turbines, fits well with this high temperature range. An embedded heat exchanger contacting the hot molten salt fluid can heat pressurized water or lower temperature steam to generate steam to drive a turbine, where inlet water pressures (non-limiting example, >24.5 MPa gauge) facilitate turbine shaft work and electricity generation. Non-limiting examples of materials that store heat at high temperature and have a >350 C temperature window of operation include: sintered bauxite particles, sodium metal, graphite, aluminium oxide, Carbonate salts, Aluminium, Copper alloys, and KBr.

Supercritical steam power cycles operating at inlet temperature of >600° C. provide great efficiency advantages as compared with steam Rankine cycles that operate between 390 to 560° C.

The process is holistic, (1) using the $O_2$ from the electrolyzer to combust biomass to make steam to load the ESS, drive rotating equipment and ultimately to co-feed water to the electrolyzer and (2) using the $NH_3$ synthesis exotherm to contribute to loading heat into a molten salt energy storage device, such that the photovoltaic panel plant need not be oversized, and the $NH_3$ synthesis can operate 24/7, which is desirable since the NH3 plant is normally a continuously operated plant with a low turn down ratio.

The $NH_3$ reactor exotherm by itself may not provide high enough temperature and perhaps not enough heat to efficiently drive a steam turbine or to make electricity for the WE during all the renewable energy deficient time periods. Supplemental concentrated $O_2$ combustion in combination with the $NH_3$ production exotherm can provide the heat needed to power the operation of the WE, when renewable energy electricity is not available due to weather or time of day. A higher temperature $NH_3$ reaction enables higher temperature heat sharing, useful for loading the molten salt ESS. If a low temperature $NH_3$ reaction is used, then the concentrated oxygen combustion processes to load the molten salt thermal energy storage is a needed method for renewable electrical input stabilization.

This is all done at a projected low cost, since: (1) molten salt thermal energy storage devices are lower CAPEX than it would be if the size of the WE plus associated PV would be increased; since (2) water is costly and scarce on location but the process gets much of its steam from biomass, since (3) PV is low cost compared with SMR in locations where there is no or high cost natural gas, since (4) extra PV may not be needed as molten salt ESS is used, and since (5) $CO_2$-free fertilizer will allow the plant owner to potentially sell agricultural products at a premium.

High concentration $O_2$ from the WE allows special process benefits, (1) high-temperature heat can be loaded to the molten salt thermal energy storage, which usually needs large, concentrated solar mirrors, by (2) the ability to oxidize Phosphorous in char to $H_3PO_4$, by (3) the ability to more easily collect $CO_2$ to make urea, by (4) the ability to effectively oxidize $NH_3$ to Nitrate to make Ammonium Nitrate.

BRIEF DESCRIPTIONS OF THE DRAWINGS

FIG. 1 provides a process flow chart view of an embodiment of the system contemplated herein.

Figure 2:
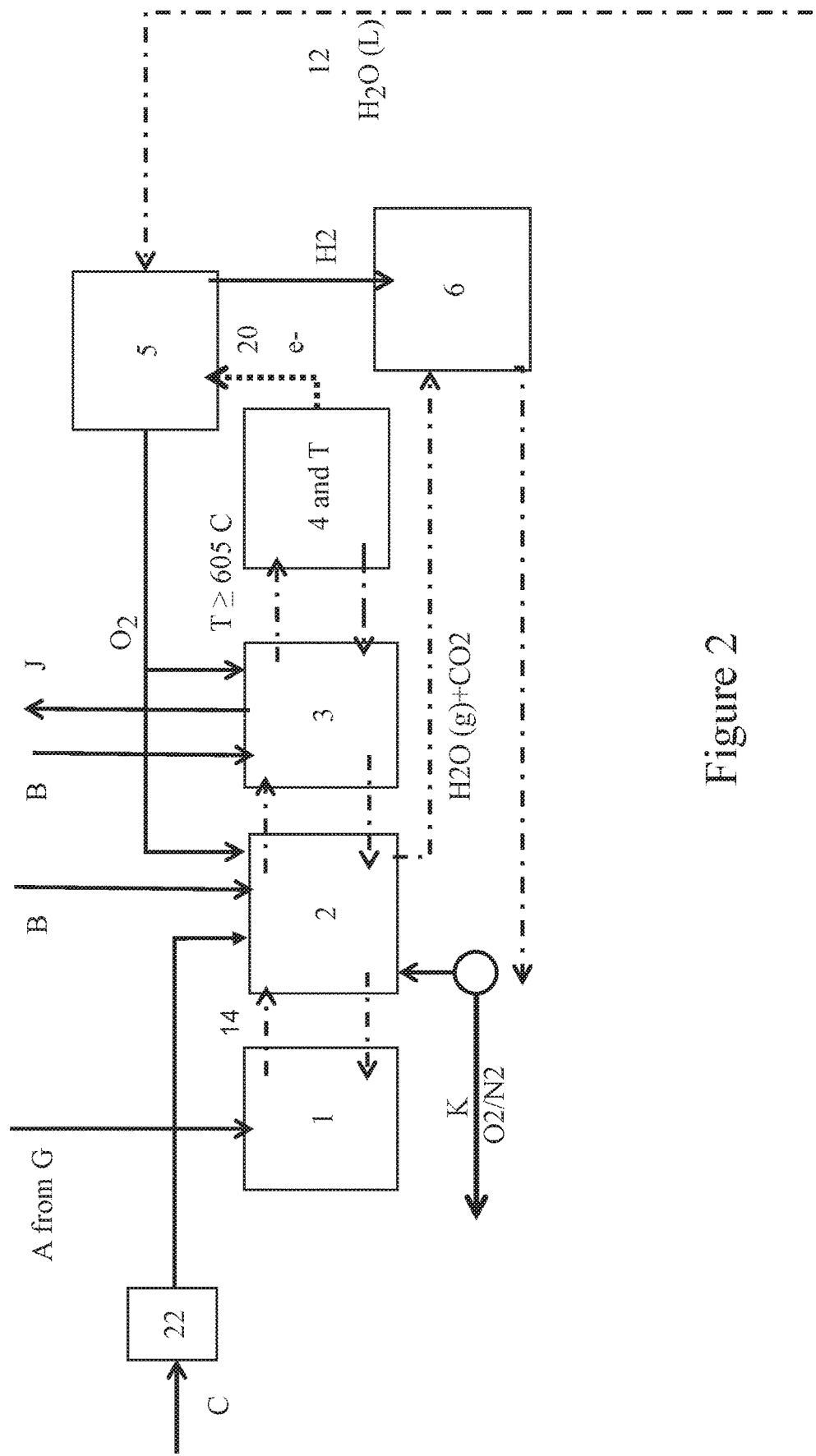

FIG. 2 provides a detail view of the process flow chart.

DETAILED DESCRIPTION

Versions of the process are described, but the main embodiment is shown in FIG. 1, which loads heat into a molten salt energy storage device by a combination steam raised from series of unit operations that progressively increase temperature: medium temperature (approx. 450 to 500° C.) $NH_3$ exotherm (for example a water tube boiler) and superheated temperature (>650° C.) biomass combustion steam generator using >94% pure O2. When needed, mostly at night, the ESS steam turbine makes electrical power to drive the WE. The preferred process does not make electric power directly from biomass in the day, rather loads the ESS when there is renewable energy and unloads the ESS when there is no renewable energy (no sunlight, no wind).

FIG. 1 shows a three-stage (Unit #1, #2, and #3) steam generation process that is used to load heat into the molten salt for 24 hours a day, or as desired, or used to provide steam to drive rotating equipment, and a molten salt thermal energy storage unit #4, which makes electricity (in Unit #3 or #4), as needed, by an associated steam turbine.

The process may also use the addition of gas to provide better oxidation characteristics. PSA off gas may provide $O_2$ enriched "air" for temperature-controlled oxidation characteristics or demineralized water may be added to the steam generating process as shown in FIG. 1, input C and demineralizer unit 22.

Photo-voltaics are used to electrically feed a water electrolyzer to make $H_2$ (and $O_2$) and the PV may be used to raise steam used to both heat molten salt based ESS and to drive rotating equipment, or the PSA and compressors may be driven by electrical motors. PV panels are low cost these days. Electricity is made with PV panels in the Middle East and Mexico at <3.5 US cents per kWh; thus PV fed electricity can compete with SMR made ammonia in cost, if the CAPEX of the overall NH3 plant is kept low, as this instant work enables.

Molten salt based ESS steam or biomass combustion exhaust may be used to drive rotating equipment (such as $H_2$ and $N_2$ compressors), or the compressors may be driven by electrical motors.

Biomass is combusted using concentrated $O_2$, preferably >94 vol. % for combustion, while the hot flue gas ($CO_2$+ steam) can add heat to the molten salt ESS unit 4 of FIG. 1 and/or generate steam. The generated steam can drive equipment and can be condensed to liquid water (to feed the water electrolyzers).

The CO2 in the flue gas (outlet stream "I" of FIG. 1) can used to produce urea. From the remaining char, Phosphorous can be extracted (outlet "J" of FIG. 1).

The steam from nearly pure $O_2$ oxidation is high-quality and uniquely high-temperature, allowing steam derived from inlet C or simply the full exhaust from the oxy-fuel combustion to feed the heat to store in molten salt, which in some systems require input heat at greater than 565° C.

Steam is separated from CO2, if needed and condensed (see Unit 8 of FIG. 1) to liquid water that is used as a cooling agent in the NH3 condenser and then fed to a water electrolyzer to make hydrogen and oxygen.

$CO_2$ in flue gas comes from plants, which extracted the $CO_2$ from the atmosphere, so it starts as $CO_2$ negative, such that if all the $CO_2$ of the biomass is released to the air, it would reach to a $CO_2$ neutral process. Only a part of the $CO_2$ made by the combustion will be emitted to the air if Urea is the product.

Some of the CO2 can be used to make Urea;

The biomass char has its phosphate content that can be extracted to use in phosphate-based fertilizer. Other sources of phosphorous may also be oxidized by the concentrated oxygen derived from the WE to make precursors to DAP >94% pure O2 oxidation may be used oxidize the Phosphorous containing compounds in char to highly oxidized P, which is needed to make DAP. The Ammonia synthesis unit derived ammonia may be used either watered-down directly as fertilizer, or as an input to make Urea using some of the oxy-fuel generated $CO_2$. The $NH_3$ exotherm can be used to feed the molten salt energy storage, thus PV oversizing to generate steam to heat the molten salt is not necessary or only minimally needed, since the oxy-fuel, enriched $O_2$ biomass combustion and/or ammonia synthesis exotherm can feed the thermal-to-electricity energy storage.

Char to diammonium phosphate (DAP) phosphorous is one of the most prevalent ingredients in the solid char generated in biomass combustion or pyrolysis. Phosphorous mild oxidation only gets to $P_2O_5$ or phosphorous acid ($H_3PO_3$). The WE generated 02 at elevated temperature with steam (water) may be used to make phosphoric acid ($H_3PO_4$) which is a precursor to diammonium phosphate ($[NH_4]_2[HPO_4]$).

The nearly pure $O_2$ has the oxidative strength to completely oxidize P (0) to P (5+) oxidation state to make the phosphorous superacid to react with water and $NH_3$ to make DAP.

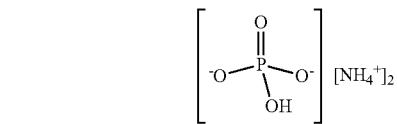

Pressurized PEM or Solid Oxide Water Electrolyzer or Alkaline Water Electrolyzer (AWE) make hydrogen for the $NH_3$ synthesis and oxygen for the oxy-fuel combustion of biomass.

The $O_2$ output of the WE may be used for the oxidation of some $NH_3$ to convert some of the NH3 to nitrate, then in combination in a water solution make ammonium nitrate

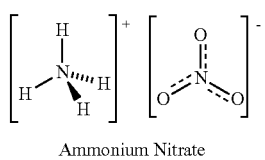

Ammonium Nitrate

The WE requires steady state power to operate also at night, when the PV is not operative. This problem is solved with molten salt thermal ESS, which can be fed from several heat sources in the process taking the burden off adding extra PV and not requiring to over-build WE equipment. The nearly pure $O_2$ allows for high-temperature combustion that makes >600° C. steam, which is useful in loading the energy storage molten salt.

A careful balance of the amount of these ingredients to make the right amount of water, steam, power, $CO_2$, $H_2$, $N_2$, and $H_3PO_4$ gets to a mix of $CO_2$-free fertilizers. The above components make $CO_2$-neutral $NH_3$, Urea, UAN, and DAP.

$N_2$ for feed to the $NH_3$ made by the air separator could be made 24 hours a day or when renewable energy output is dissipated by combustion steam or the thermal ESS electricity. $H_2$ production, before this work, appears to require an oversized WE to somehow be operate at increased MW (more than doubling the WE, ASU and PV CAPEX) in the PV operation time. A pressurized ammonia synthesis reactor with a recycle loop as shown in FIG. 1 may be used to make ammonia, separate the ammonia product, as indicated in Unit #9 of FIG. 1, and return unreacted N2/H2 to the feed of the reactor as shown in Stream #15. Heat from the ammonia reactor, shown as Unit #10 in FIG. 1 is moved to the steam generator as indicated by Stream #G to A and enters the lower temperature steam generator unit marked as Unit #1 in FIG. 1. The heat by way of steam makes its way to the molten salt thermal energy storage Unit #4 by the steam piping as indicated by the dashed-line arrows in FIG. 1, including Stream #14 in FIG. 1 that connects the units #1, #2, #3 to #4.

Instead of intensively operating the WE and ASU double in the day it can operate near steady state all day while the PV is not increased in size but the molten salt is heated.

Molten salt energy storage is common for solar energy storage in CSP equipment and practical. Heat can be provided to the molten salt ESS in the renewable ammonia process from: nearly pure $O_2$ combustion of biomass, enriched $O_2$ from the PSA exhaust combustion, and/or the exotherm from the $NH_3$ synthesis.

This apparatus and method allow that the photovoltaic plant need not be oversized but have thermal energy storage fed by heat to provide power when the renewable plant is not producing power. In this way the combustion process also makes the water for the WE and cooling processes, water which is otherwise scarce. Electricity may be generated by the thermal energy storage at night-time or when neither wind turbines nor solar panels are generating electricity. The oxy-combustion process may make steam and heat 24/7, but only when the renewable energy is not available (no wind no sunlight) would the ESS device convert the heat to power to drive the WE and ASU.

AWE instead of PEM electrolyzers can be used when energy storage is added to the system, since no special capability to follow photovoltaic load changes are needed, if an ESS is used instead of a double sized AWE. The molten salt built in energy storage allows the process to use less MW of AWE equipment instead of doubling the AWE or using costly PEM electrolyzers. Energy storage allows the process to take advantage of the ability of AWE equipment that have large industrial capacity, such as, 300 MW electrolyzers, which requires AWE instead of PEM.

Producing the $H_2$ and $N_2$ simultaneously instead of sending $H_2$ to storage, makes it easier to use the same compressors for the $H_2/N_2$ mixture in an efficient manner.

The method to load the energy storage device may or may not be by extra PV capacity, but includes nearly pure $O_2$ combustion of biomass and/or the exotherm from the $NH_3$ synthesis.

Hydrogen Storage, unlike the general assumption in the industry, is not needed, no excessively large hydrogen storage device or tank farm is needed to hold $H_2$ for night time usage, since the AWE will operated day and night. Some amount of $H_2$ storage is needed in all processes and $H_2$ will be stored to buffer the AWE operation.

A Pressure Swing Air Separation Unit (PSA), the nitrogen required is provided by a PSA, which separates the air into pure nitrogen and oxygen-enriched air. A cryogenic air separation unit may be used but may not be required since the required if small ammonia plants are desired where the flowrate of nitrogen is still in the range of PSA and oxygen is not a product so that CAPEX of air separation can be saved.

If the PV is oversized it can contribute to loading heat to the ESS (Unit #4) in FIG. 1. In FIG. 1 the PV may or may not be oversized.

The molten salt ESS provides more benefit when it is above 550° C., such that the NH3 exotherm between 400 and 523° C. can be a first stage for steam generation and the oxy-fuel biomass combustion at above 605° C. can be a final stage of steam generation used to add heat to the molten salt at the required temperature level.

The >94% pure $O_2$ biomass combustion allows the process to get easily to high temperature heat which is beneficial to loading heat into a molten salt energy storage device. This could not be easily done with air combustion, due to the concerns of NOx production and $N_2$ diluent in the oxidation medium.

Although phosphorous reaped is small compared to $NH_3$ made, some DAP can be generated together with $NH_3$, Urea and UAN.

The oxygen generated from the water electrolyzer, which is often wasted, is used for oxy fuel generation of water, high-grade heat, phosphorous, $CO_2$ for urea, and the oxidation of $NH_3$ to make nitrate to generate UAN in a holistic apparatus.

FIG. 1 makes use of $O_2$ emitted from the water electrolyzer (WE) and may use enriched $O_2$ emitted from an ASU (7 in FIG. 1) or PSA to make steam hot enough to "load heat" into a molten salt energy storage device 4 in FIG. 1 which includes a turbine to generate electricity from steam generated by the stored heat energy. Molten ESS devices that produce steam driven power usually benefit from an operation temperature more than 550° C. and the oxygen stream emitted from the WE can easily provide such heat by controlled oxy-fuel combustion.

The Salt thermal ESS produce electricity (20 in FIG. 1) at the time periods that the renewable energy source cannot. For example, a combination of wind turbines and photovoltaics (indicated by 11 in FIG. 1) have difficulty providing steady electricity when the sun is down. During that time period, the Molten Salt ESS can generate electricity to drive the electrolyzer (designated at #5 in the figure). FIG. 1 shows that some steam can be used to drive the $H_2$ and $N_2$ compressors (indicated by 6 in FIG. 1) or electricity from the molten salt ESS can be used to drive these turbines.

Biomass is assumed available if user is an agricultural setting and indicated as a feed to the process by B in FIG. 1. But in many Agricultural settings, water is a prized commodity, so we "recycle" water by condensing (unit operation #8 in FIG. 1) it from flue gas during enriched oxygen combustion of biomass. Municipal or industrial waste or any hydrogen-containing fuel may also be used as the fuel source for the oxy-fuel combustion. Not indicated in FIG. 1 is the exhaust of the concentrated oxygen combustion of biomass may be recycled to the steam generation or power generation process, as a diluent, to control the temperature of the concentrated oxygen steam generator or the steam turbine.

The concentrated oxygen steam generator is indicated to use at least three stages, indicated by Unit operation 1, 2 and 3. Unit operation 1 uses the heat from the ammonia synthesis exotherm (Stream A to G). The interconnecting steam lines between Units #1, #2, #3, #4 are designated by the dashed lines between the units including Stream #14. Unit operation 2 may moderate the concentrated oxygen combustion of biomass by the introduction of Demineralized water, introduced at C and demineralized at 22 or by recycled combustion gas. Unit operation 3 is the high temperature concentrated oxygen combustion of biomass, using less diluent.

Water that enters a water electrolyzer has high standards of purity. Therefore it is generally preferred to use steam that is derived by D.I. water entering at C or water that is derived from concentrated oxygen combustion of biomass and cleaned by be used. Unit operation 3 does not show the detail, but indicates that the ash and char must be removed at J. However, the exhaust heat from the combustion, including the heated $CO_2$ can be used to inject heat into the Molten Salt ESS. Unit operation 8 indicates that low temperature steam (LTS) contaminated with $CO_2$ must undergo a separation process before any such water could be fed to a WE, shown as 5. Other components of FIG. 1 are as follows: 1—$NH_3$ Exotherm Steam Generator; 2—Temp-controlled $O_2$ Steam Generator; 3—Oxy-fuel Steam Generator; 4—Salt ESS and night Turbine; 5—Water Electrolyzer; 6—$H_2/N_2$ Compressor(s); 7—PSA or Cryogenic ASU; 8—Air or sea-cooled steam condenser; 9—NH3 cooling and separation; 10—NH3 Synthesis; 11—PV and/or Wind Turbine; 12—$H_2O$ (L); J—$X^{2+}[HPO_4]^{2-}$, where $X^{2+}$ indicates 2H+, or 2NH4+ or 2Na+, or 2K+ or Ca2+ or other suitable cations; K—O2/N2, PSA or ASU output 13—$O_2$; 14—a series of steam lines connecting the stages of the steam generator; 15—Recycle; 19 and 20—Electrical Current; 21—DeNOx; B—Biomass; G—Reaction Exotherm; H—NH3 to storage or urea or nitrate or DAP; A—NH3-Exotherm; and E,F—Sun and wind. A one-pass ammonia reactor usually does not provide sufficient conversion of N2 and H2 to NH3, therefore stream #15 recycles unconverted N2 and H2 to the front of the ammonia reactor.

FIG. 2 is a detail of FIG. 1. The components of FIG. 2 are as follows: 1—$NH_3$ Exotherm Steam Generator; 2—Oxygen waste combustion-controlled temperature with limited water injection; 3—Oxygen combustion for pressurized steam generation; 4—up to 605° C. steam-heated Salt Energy Storage System that is converted to electricity at night by steam turbine/generator; 5—Water Electrolyzer either PEM up to 35 bar or Alkaline; 6—$H_2/N_2$ Compressor(s); 20—Electrical Current; A—NH3-Exotherm; B—Biomass; C—$H_2O$ for steam generator temperature control; J—$X^{2+}[HPO_4]^{2-}$; 12—$H_2O$ (L), where $X^{2+}$ indicates 2H+, or 2Na+, or 2K+ or Ca2+ or other suitable cation; K—O2/N2, PSA or ASU output and 22—Demineralization process. In some process variations, especially if a cryogenic air separator is used, the output enriched oxygen may be sent to the staged, oyx-fueled steam generator, while in other process variations the enriched but N2 laden output of the PSA may be simply exhausted to atmosphere as shown in Stream #K of FIG. 1. When urea is a product of interest, then it is better not to mix nitrogen from air with the oxy-fueled combustion, in order to separate nitrogen from CO2. Further nitrogen in high temperature combustion would make un-wanted NOx.

The air separator and compressors could be electrically driven, in which case heat stored in the molten salt is used for power generation or steam-driven equipment.

At the bottom right of FIG. 1, the exotherm from the NH3 process is sent to the top left part of the process flow diagram, where it is written: "G to A".

The process has two sources of electricity to operate the water electrolyzer: the renewable energy processes, such as PV, by day, and the molten salt thermal ESS heat is converted to electricity at night.

In FIG. 1 char from the biomass combustion contains P (5+) that can be converted to DAP with $NH_3$. Not shown in FIG. 1 is some of the $CO_2$ can be used to make urea. Not shown in FIG. 1 is $NH_3$ may be oxidized to nitrate to make UAN, using either oxy-fuel or enriched $O_2$ from an air separator (PSA or cryogenic ASU).

Only with nearly pure $O_2$ can biomass combustion temperature be high enough to feed heat into the high temperature molten salt thermal ESS. High temperature steam turbine production of power from the molten salt ESS operates at higher efficiency than a process that would only use air for combustion. Phosphorous can be effectively converted to DAP if concentrated $O_2$ is used and $NH_3$ may be made effectively to Nitrate to make ammonium nitrate by concentrated $O_2$ processes.

Another embodiment of the process would be like FIG. 1, not mixing the gas phases of the oxy-fuel with $N_2$ from air, rather using water as a combustion diluent. Therefore the option to use the oxygen concentrated side of a PSA to combust is not preferred compared with using concentrated oxygen with either recycled exhaust gas or demineralized water.

In this regard diluted oxygen followed by oxy-fuel combustions heat may be in parallel gas phase feeding and in series steam flow as the water progresses from LTS to MTS to HTS to supercritical in order to heat the molten salt as shown in FIG. 1, since it is also preferred not to have any PSA nitrogen enter the oxy-fuel combustor, to minimize NOx production.

High temperature pure oxygen combustion usually requires special materials, but in this design we only need to get to combustion temperatures high enough to load the molten salt with heat, approximately >600° C. The process of FIG. 2 indicates that either demineralized water or recycled combustion exhaust may be used to control the temperature to the desired levels and deliver 605° C.

Molten salt energy storage is one of the most inexpensive, low cost ESS systems. The CAPEX for the Molten Salt (not including steam turbine) can be ⅒ of a lithium ion battery. The present work adds the molten salt at very low CAPEX instead of doubling the electrolyzer plus increasing the photovoltaic panels or using electric battery storage, as all these other options would add burdensome cost to the ultimate fertilizer produced.

Many very large-scale molten salt-based energy storage plants are in operation, including: Solana in Ariz., USA at 250 MW (4670 $MWh_{th}$); Crescent Dunes, Nev., USA at 110

MW, and many plants in Spain as large as 1 GW. To make a 350 MT/d NH3 plant using this design we would need about 165 MW×15 hours=2475 MWh$_e$, which is on par than the Solana and Crescent Dunes molten salt plants since to get from thermal to electric is about 45% efficiency.

List of acronyms: Low Temperature Steam (LTS); Water Electrolyzer or water electrolysis (WE); Medium Temperature Steam (MTS), High Temperature Steam (HTS); Energy Storage System (ESS); Thermal Energy Storage (TES), when associated with a steam turbine and electricity generator TES treated as equivalent to ESS in this document; Capital Expenditure (CAPEX); Pressure Swing Absorber (PSA); Air Separation Unit (ASU); Ammonium Nitrate with Urea in water solution (UAN); Diammonium Phosphate (DAP); photovoltaic panels (PV); Concentrated Solar Power (CSP); Polymer Electrochemical Membrane based electrolyzer (PEM); Megawatts (MW) and Alkaline Water Electrolyzer (AWE).

What is claimed is:

1. A system for production of ammonia comprising:
   a renewable energy source;
   an energy storage system comprising a heat storage unit operable to store heat which is usable to generate steam and electricity to drive process equipment during a time period when the renewable energy source is deficient to drive the process equipment on its own;
   wherein the process equipment comprises a water electrolyzer for production of concentrated oxygen and hydrogen, an air separation unit for production of nitrogen and oxygen; and
   an ammonia reactor operable to produce heat and ammonia using nitrogen from the air separation unit and hydrogen from the water electrolyzer; and
   a steam generator operable to combust a fuel with a portion of the concentrated oxygen and/or operable to use the exotherm of ammonia production to produce steam; and
   wherein the energy storage system is a molten salt thermal energy storage device, and further comprising a steam turbine connected to the molten salt thermal energy storage device, and an electrical generator operably connected to the steam turbine.

2. The system of claim 1 wherein the renewable energy source is at least one of a solar power electricity generator or a wind turbine.

3. The system of claim 2 wherein the process equipment further comprises one or more compressors, and wherein the water electrolyzer is one of a PEM, alkaline or solid oxide device.

4. The system of claim 1 wherein the thermal storage salt is molten at the temperature of the steam generator output.

5. The system of claim 1 wherein the fuel is at least one of hydrogen-containing fuel, a biomass or a municipal waste.

6. The system of claim 1 wherein the fuel is a biomass, and wherein a steam generated by the steam generator is at a temperature high enough to enable steam turbine power production, but not hotter than a top temperature limit of the molten salt thermal energy storage device.

7. The system of claim 1 wherein the steam generator is a staged steam generator comprising a first stage of the steam generator which utilizes an exotherm heat generated from an ammonia reactor, a second stage of the steam generator which utilizes heat generated from a combustion of a fuel with a concentrated oxygen from the air separation unit with injection of water or recycled exhaust gas to moderate a temperature, and a third highest temperature stage of the steam generator which utilizes heat generated from the combustion of a fuel with a quantity of concentrated oxygen from the water electrolyzer.

8. A renewable ammonia production system that requires only minimal intermediate storage of hydrogen comprising:
   a renewable energy source;
   a water electrolyzer operable to generate concentrated oxygen and hydrogen from water;
   a molten salt energy storage device;
   a steam generator operable to accept heat from a quantity of concentrated oxygen from the water electrolyzer combusting with a fuel and/or accept heat from the exothermic production of ammonia to produce steam, the steam providing a heat energy to the molten salt energy storage device;
   an air separation unit operable to generate nitrogen and oxygen from air;
   one or more compressors; and
   an ammonia reactor operable to produce heat and ammonia using nitrogen from the air separation unit and hydrogen from the water electrolyzer; and
   wherein a power for operation of the water electrolyzer, compressors and air separation unit comes from at least one of the renewable energy source or the molten salt energy storage device.

9. The system of claim 8 wherein the renewable energy source is at least one of a solar power electricity generator or a wind turbine;
   and wherein the fuel is at least one of a biomass, a municipal waste or a hydrogen-containing fuel.

10. The system of claim 8 wherein the steam generator is a staged steam generator comprising a first stage of the steam generator which utilizes heat generated from the ammonia reactor, a second stage of the steam generator which utilizes heat generated from a combustion of the fuel with a concentrated oxygen moderated in temperature by one of injected water, exhaust recycle or a nitrogen-oxygen mixture, and a final stage steam generator which utilizes heat generated from the combustion of the fuel by the quantity of concentrated oxygen from the water electrolyzer wherein heat from the generated steam is loaded into the molten salt energy storage device for later use.

11. The system of claim 8 wherein a steam generator comprises an additional stage operable to accept heat generated by the renewable energy source to produce steam.

* * * * *